United States Patent [19]

Ammermann et al.

[11] Patent Number: 4,604,429
[45] Date of Patent: Aug. 5, 1986

[54] AMMONIUM SALTS OF POLYMERIC ACIDS, THEIR PREPARATION AND USE AS FUNGICIDES

[75] Inventors: Eberhard Ammermann; Ernst Buschmann, both of Ludwigshafen; Gregor Ley, Wattenheim; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 672,699

[22] Filed: Nov. 19, 1984

[30] Foreign Application Priority Data

Nov. 19, 1983 [DE] Fed. Rep. of Germany ....... 3341829

[51] Int. Cl.$^4$ .................... C08F 30/00; C08F 130/08; C08F 230/08
[52] U.S. Cl. .................... 525/326.6; 525/327.5; 525/327.6; 525/328.2; 525/328.4; 525/328.5; 525/328.7; 525/328.9; 525/329.2; 525/329.4; 525/329.5; 525/329.8; 525/329.9; 525/330.4; 525/330.5; 525/331.5; 525/333.5; 525/333.6; 525/349; 525/375
[58] Field of Search ............... 525/326.6, 328.2, 328.5, 525/328.7, 329.2, 329.4, 329.5, 329.8, 329.9, 330.4, 330.5, 331.5, 327.6, 328.4, 333.5, 333.6, 349, 375, 327.5, 328.9

[56] References Cited

U.S. PATENT DOCUMENTS 4,402,894 5/1980 Pfiffner .................... 424/248.4

FOREIGN PATENT DOCUMENTS 2700680 7/1978 Fed. Rep. of Germany .
1525300 12/1974 United Kingdom .

Primary Examiner—Joseph L. Schofer
Assistant Examiner—J. M. Reddick
Attorney, Agent, or Firm—Keil & Weinkauf

[57] ABSTRACT

Fungicides containing ammonium salts of polyacids of the formula

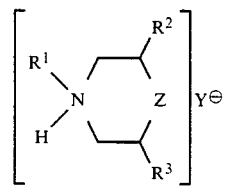

where $R^1$ is alkyl, cycloalkyl, cycloalkylalkyl or aralkyl, $R^2$ and $R^3$ are each hydrogen, hydroxyl, $CH_2OH$ or $C_1$–$C_3$-alkyl, Z is $CH_2$, O, S, CO or $(CH_2)_2$ and Y is an anion of a copolymeric acid.

3 Claims, No Drawings

AMMONIUM SALTS OF POLYMERIC ACIDS, THEIR PREPARATION AND USE AS FUNGICIDES

The present invention relates to ammonium salts of polymeric acids, in particular salts from cyclic amines, fungicides which contain these substances, processes for their preparation, and methods for controlled fungi with the aid of these compounds.

It has been disclosed that cyclic amines and their salts with monomeric acids can be used as fungicides (DE-11 64 152, DE-26 56 757 and DE-27 52 096). The fungicidal activity, the duration of action and the toleration of these substances by plants are insufficient in many cases.

We have found that ammonium salts of polymeric acids of the formula

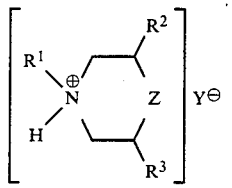

where $R^1$ is alkyl, cycloalkyl, cycloalkylalkyl, or aralkyl, $R^2$ and $R^3$ are independently hydrogen, OH, $CH_2OH$ or $C_1$–$C_3$-alkyl, Z is $CH_2$, O, S, CO or $(CH_2)_2$ and $Y^\ominus$ is an anion of copolymeric acid based on a carboxylic, sulfonic or phosphonic acid capable of free radical polymerization and another polymerizable monomeric compound, possess substantially greater activity than the conventional cyclic amines and their salts with monomeric acids. The novel salts are water-soluble or dispersible in water.

$R^1$ has, for example, 12 to 14 carbon atoms and may be $C_{12}$–$C_{14}$-alkyl, such as n-dodecyl, isotridecyl, n-$C_{14}$–$H_{29}$ or 1,5,8-trimethyldecyl, or cyclododecyl, 3-p-tert.-butylphenyl-2-methylpropyl or 3-(4-tert.-butylcyclohexyl)-2-methylpropyl.

$R^2$ and $R^3$ are each hydrogen, methyl, ethyl, propyl, OH or $CH_2OH$.

Examples of acidic monomeric building blocks for the preparation of the anions Y are acrylic acid, methacrylic acid, maleic acid, maleic anhydride, vinylsulfonic styrenesulfonic acid, allylsulfonic acid, methallylsulfonic acid, acrylamido-2-methylpropanesulfonic acid, vinylphosphonic acid and their salts, and mixtures of these. Examples of other monomeric compounds are commercial vinyl and acrylic monomers, eg. styrene, vinyl acetate, vinyl propionate, vinyl chloride, acrolein, methacrolein, acrylonitrile, methacrylonitile, (meth)acrylamide and its derivatives, and malonates, fumarates and (meth)acrylates, preferred compounds among the copolymerizable esters being those which also contain free OH groups or polyether groups in the alcohol component, eg. hydroxyalkyl esters where the alkyl radical of the (meth)acrylic acid is of 2 to 8 carbon atoms, or compounds of the formula

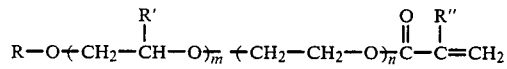

where R is hydrogen, $C_1$–$C_{20}$-alkyl or $C_1$–$C_{18}$-alkylphenyl, R' is methyl or ethyl, R" is hydrogen or methyl and n and m are independently numbers from 0 to 100.

The lastmentioned monomeric building blocks, in particular, contribute substantially to the solubility or dispersibility of the novel salts in water.

Preferred copolymers are those of an acid, in particular vinylphosphonic acid or acrylamido-2-methylpropanesulfonic acid, with an acrylate where the alcohol radical of the ester contains a higher alkyl radical, eg. $C_{16}$–$C_{20}$-alkyl, in particular $C_{18}$-alkyl, and from 60 to 100, in particular 80, ethylene oxide groups ($CH_2$–$CH_2$–O). The ratio of the monomers (acid:ester) in the mixture can vary within wide limits and can be, for example, from 20:80 to 80:20, in particular from 33:67 to 67:33, parts by weight.

The active ingredients of the formula I contain an asymmetric carbon atom in the aliphatic or cycloaliphatic radicals $R^1$ and can occur in the form of various enantiomers or diastereomers. The invention embraces the pure enantiomers and diastereomers, as well as their mixtures.

Salts with the following amines are preferred: N-n-dodecyl-2,6-dimethylmorpholine, N-isotridecyl-2,6-dimethylmorpholine, N-cyclododecyl-2,6-dimethylmorpholine, N-(3-p-tert.-butylphenyl-2-methylpropyl)-piperidine and N-(3-p-tert.-butylphenyl-2-methylpropyl)-2,6-cis-dimethylmorpholine.

The copolymeric acids can be prepared by a conventional free radical polymerization process, in the absence of a solvent, in solution, in emulsion or in suspension, using a conventional initiator (for example an inorganic or organic peroxide, a compound containing a labile C—C bond or an azo compound) and assistants, such as emulsifiers, protective colloids and regulators, for example labile chlorine or bromine compounds, alcohols or mercaptans. Such regulators are employed in order to lower the degree of polymerization. This is important, for example, when the novel salts are used in the form of their solutions, in order to keep the viscosity of the solutions very low so that they are easy to handle.

The Fikentscher K value can be used as a measure of the degree of polymerization of the copolymeric acids (Cellulose Chemie, 13 (1932), 48–64 and 71–74). The K value is measured in a 1% strength by weight aqueous solution at 25° C.; $K = 10^3 k$. The K values of the acids determined in this manner are, for example, from 10 to 50, preferably from 10 to 30.

Reaction of the basic active ingredients with the polymeric acids to give the novel salts is carried out, for example, when the polymerization is complete, simply by mixing the ready-prepared components; other formulation assistants, such as emulsifiers, wetting agents, carriers, stabilizers and solvents, can also be added at this stage. In certain cases, the salt is advantageously formed before the polymerization, the base being reacted with the acidic monomers. A precondition for this is that the resulting monomeric salt is copolymerizable, and the active ingredient is stable under polymerization conditions and is free from impurities which could present problems in the subsequent copolymerization.

When dissolved in water, most of the novel salts give stable spray liquors even without the use of further formulation assistants, the spray liquors drying on the plant substrates to give polymeric coatings which contain the active ingredient, exhibit good adhesion and are well tolerated by plants. The pH of the aqueous solutions of the salts is from 6 to 8. In addition to containing the novel salts, the fungicides can contain the free amines from which the salts are derived.

The Examples which follow illustrate the preparation of the novel salts. Parts and percentages are by weight.

EXAMPLE 1

70 parts of water, 70 parts of acrylamido-2-methylpropanesulfonic acid, 140 parts of isopropanol, 140 parts of an acrylate of the formula II, where R is $C_{18}$-alkyl, m is 0 and n is 80, 4.2 parts of hydroxylammonium sulfate and 7 parts of azobisisobutyronitrile are introduced into a polymerization reactor equipped with a nitrogen inlet, a thermometer, a stirrer and a reflux condenser, and the mixture is heated at 80° C. using a water bath. The mixture is kept at this temperature under a gentle stream of nitrogen for 3 hours, after which it is cooled. A clear polymer solution having a solids content of 50% and a K value of 26 is obtained.

29 parts of the active ingredient N-(3-p-tert.-butylphenyl-2-methylpropyl)-2,6-cis-dimethylmorpholine (fenpropimorph) are added slowly, in the course of about 1 hour, while stirring and at 40° C. to 100 parts of the polymer solution prepared as described above, in a stirred flask over a water bath. Stirring is continued for about a further hour, after which the mixture is cooled to give a clear solution of the salt which contains 22.5% of active ingredient and gives a stable spray liquor when diluted with water.

EXAMPLE 2

105 parts of water, 70 parts of vinylphosphonic acid, 105 parts of isopropanol and 140 parts of the acrylate described in Example 1 and 7 parts of azobisisobutyronitrile are introduced into the apparatus described in Example 1. The procedure described in Example 1 is followed, and a polyacid solution having a solids content of 50.4% and a K value of 21 is obtained.

As described in Example 1, 45 parts of the active ingredient fenpropimorph are added to 100 parts of the polyacid solution prepared as described above. The resulting solution of a salt of a polyacid contains 31% of active ingredient and gives a stable spray liquor when diluted with water.

EXAMPLE 3

35 parts of water, 35 parts of isopropanol, 70 parts of vinylphosphonic acid, 140 parts of the acrylate described in Example 1 and 7 parts of azobisisobutyronitrile are introduced into the apparatus described in Example 1. Using the process described in Example 1, a polyacid solution having a solids content of 73% and a K value of 20 is obtained.

As described in Example 1, 68 parts of the active ingredient fenpropimorph are added to 100 parts of the polyacid solution prepared as described above. A solution containing 40% of active ingredient is obtained.

EXAMPLE 4

35 parts of water, 35 parts of isopropanol, 140 parts of vinylphosphonic acid, 70 parts of the acrylate described in Example 1 and 7 parts of azobisisobutyronitrile are reacted in the apparatus described in Example 1 to give a polyacid solution having a solids content of 74% and a K value of 16.

As described in Example 1, 100 parts of a solution prepared as described above are reacted with 67 parts of the active ingredient fenpropimorph to give a solution of a salt of a polyacid, the solution containing 40% of active ingredient and giving a stable spray liquor when diluted with water.

EXAMPLE 5

As described in Example 1, a mixture of 14.5 parts of fenpropimorph and 14.5 parts of tridemorph (N-isotridecyl-2,6-dimethylmorpholine) is added slowly, in the course of about 1 hour, while stirring and at 40° C., to 100 parts of the polymer solution prepared as described in Example 1. Stirring is continued for about a further hour, after which the mixture is cooled to give a clear solution which contains about 22.5% by weight of active ingredient and gives a stable spray liquor when diluted with water.

EXAMPLE 6

The procedure described in Example 5 is followed, except that a 1:1 mixture of the active ingredients fenpropimorph and dodemorph (N-cyclododecyl-2,6-dimethylmorpholine) is used. The preparation obtained also gives a stable spray liquor when diluted with water.

The novel salts, and fungicides containing them, are particularly suitable for combatting plant diseases, e.g., *Erysiphe graminis* in cereals, *Erysiphe cichoriacearum* in cucurbits, *Podosphaera leucotricha* in apples, *Uncinula necator* in grapes, *Erysiphe polygoni* in beans, *Sphaerotheca pannosa* in roses, *Microsphaera querci* in oaks, *Botrytis cinera* in strawberries and grapes, *Mycosphaerella musicola* in bananas, Puccinia species (rusts) in cereals, *Uromyces appendiculatus* and *U. phaseoli* in beans, *Henuleia vastatrix* in coffee, and *Rhizoctonia solani*. They have a systemic action, and are taken up both by the roots and foliage, and translocated in the plant tissue.

When the novel active ingredients are used to protect plants against fungus infection, application rates are from 0.025 to 5 kg of active ingredient per hectare. For the surface protection of trees and fruit, the active ingredient may also be employed in conjunction with plastics dispersions in concentrations of 0.1 to 95%, based on the weight of the dispersion. The fungicides generally contain from 0.1 to 95, and preferably from 0.5 to 90, wt% of active ingredient.

The active ingredients may suppress simultaneously the growth of two or more of the said fungi, and are well tolerated by plants. Some of the active ingredients have curative properties, i.e., the agents may also be successfully applied after infection of the plants by the pathogen.

The novel active ingredients may also be mixed and applied with other active ingredients, e.g., herbicides, insecticides, growth regulators, other fungicides and fertilizers. When mixed with other fungicides, the spectrum of fungicidal action is in many cases increased; with a number of these fungicidal compositions, synergistic effects also occur, i.e., the fungicidal action of the combination product is greater than the effect of the individual components added together. Examples of fungicides which can be combined with the novel compounds are as follows:

sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisthiocarbamate)
and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidine-methanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropyl-carbamoylhydantoin
N-(3,5-dichlorophenyl)-1,2-dimethyl-cyclopropane-1,2-dicarboximide.

The novel active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure a fine distribution of the novel active ingredient. Solution or dispersion in water is preferred.

For the preparation of solutions, emulsions, pastes and oil dispersions to be sprayed direct or after emulsification in water, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octyphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers, such as ammonium sulfate, ammonium phosphate, ammonium nitrate, and ureas, and vegetable products such as grain flours, bark meal, wood meal, and nutshell meal, cellulosic powders, etc.

The following experiment illustrates the fungicidal action of the novel compounds.

EXPERIMENT 1

Winter wheat of the "Caribo" variety was sown in the fall in plots 1.5 m² in size in the open. In the following April the plots were so heavily afflicted by spontaneous infection with wheat mildew (*Erysiphe graminis* var. tritici) as to earn the mark 4 in the assessment scale below of the Biologische Bundesanstalt (Federal German Biological Institute) Brunswick. It was at this point that treatment was carried out: 250 ml of aqueous spray liquor was applied to each plot by means of a mobile boom sprayer. Two repeats were run for each concentration. Assessments were made at 10-day intervals. The values given are averages from 3 individual figures.

Assessment scale (after Federal German Biological Institute)
1: no attack
2: up to 2.5% attack
3: 2.5 to 5% attack
4: 5 to 10% attack
5: 10 to 15% attack
6: 15 to 25% attack
7: 25 to 35% attack
8: 35 to 67.5% attack
9: 67.5 to 100% attack The results of this experiment show that the novel salts according to Examples 3 and 4, applied as 0.075 to 0.1125% (calculated as fenpropimorph) spray liquors, had, after 10, 20, 30 and 40 days, a better fungicidal action (1.0–2.7) than fenpropimorph in its commercial formulation (1.7–4.3).

We claim:

1. An ammonium salt of a polymeric acid of the formula

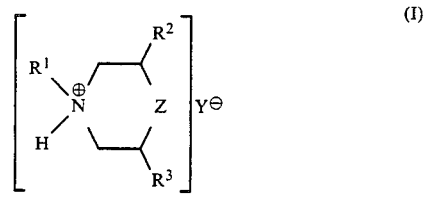

where $R^1$ is alkyl, cycloalkyl, cycloalkylalkyl or aralkyl, $R^1$ having 12–14 carbon atoms, $R^2$ and $R^3$ are each hydrogen, OH, $CH_2OH$ or $C_1$–$C_3$-alkyl, Z is $CH_2$, O S, CO, or $(CH_2)_2$ and Y is an anion of a copolymeric acid based on acrylic acid, methacrylic acid, maleic acid, maleic anhydride, vinylsulfonic acid, styrenesulfonic acid, allylsulfonic acid, methallylsulfonic acid, acrylamido-2-methylpropanesulfonic acid, vinylphosphonic acid and their salts, or mixtures thereof, and another monomeric compound selected from the group consisting of vinyl acetate, vinyl propionate, vinyl chloride, acrolein, methacrolein, acrylonitrile, methacrylonitrile, (meth)acrylamide and its derivatives, and malonates, fumarates and (meth)acrylates, said copolymeric acid having a K-value of from 10–50.

2. An ammonium salt as set forth in claim 1, containing a cation of N-n-dodecyl-2,6-dimethylmorpholine, N-iso-tridecyl-2,6-dimethylmorpholine, N-cyclododecyl-2,6-dimethylmorpholine, N-(3-p-tert-butylphenyl-2-methylpropyl)-piperidine or N-(3-p-tert-butylphenyl-2-methylpropyl)-2,6-cis-dimethylmorpholine.

3. An ammonium salt as set forth in claim 1, wherein the salt contains a cation of N-(3-p-tert-butylphenyl-2-methylpropyl)-2,6-cis-dimethylmorpholine and wherein Y is an anion of a copolymeric acid based on vinylphosphonic acid, acrylamido-2-methyl-propanesulfonic acid and an acrylate of the formula II

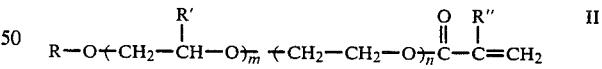

where R is $C_{18}$-alkyl, R" is hydrogen, m is 0 and n is 80.

* * * * *